(12) United States Patent
Golz-Berner et al.

(10) Patent No.: US 7,217,423 B2
(45) Date of Patent: May 15, 2007

(54) REVITALISING ACTIVE COMPLEX FOR THE SKIN

(75) Inventors: Karin Golz-Berner, Monaco (DE); Leonhard Zastrow, Monaco (DE)

(73) Assignee: Coty B.V. (NL)

( * ) Notice: Subject to any disclaimer, the term of this patent is extended or adjusted under 35 U.S.C. 154(b) by 644 days.

(21) Appl. No.: 10/250,392

(22) PCT Filed: Jan. 29, 2002

(86) PCT No.: PCT/DE02/00363

§ 371 (c)(1),
(2), (4) Date: Jun. 30, 2003

(87) PCT Pub. No.: WO02/060394

PCT Pub. Date: Aug. 8, 2002

(65) Prior Publication Data

US 2004/0052749 A1    Mar. 18, 2004

(30) Foreign Application Priority Data

Feb. 2, 2001   (DE) ................. 101 06 288

(51) Int. Cl.
*A61K 6/00*     (2006.01)
*A61K 8/02*     (2006.01)
*A61K 8/18*     (2006.01)
*A61K 9/127*    (2006.01)

(52) U.S. Cl. ............. 424/401; 424/59; 424/450
(58) Field of Classification Search ............. None
See application file for complete search history.

(56) References Cited

U.S. PATENT DOCUMENTS

| | | | | |
|---|---|---|---|---|
| 5,391,373 | A | | 2/1995 | Mausner ............. 424/401 |
| 5,637,318 | A | * | 6/1997 | Gross et al. ............. 424/450 |
| 5,643,601 | A | * | 7/1997 | Gross et al. ............. 424/450 |
| 5,686,102 | A | * | 11/1997 | Gross et al. ............. 424/450 |
| 5,885,564 | A | * | 3/1999 | Zastrow et al. ............. 424/74 |
| 5,919,490 | A | * | 7/1999 | Zastrow et al. ............. 424/647 |
| 5,961,988 | A | * | 10/1999 | Zastrow et al. ............. 424/400 |
| 2003/0170333 | A1 | * | 9/2003 | Golz-Berner et al. ......... 424/777 |

FOREIGN PATENT DOCUMENTS

WO       01/00203       1/2001

* cited by examiner

*Primary Examiner*—Sreeni Padmanabhan
*Assistant Examiner*—Marina Lamm
(74) *Attorney, Agent, or Firm*—Akerman Senterfitt

(57) ABSTRACT

The invention relates to a revitalizing active complex for the skin and cosmetic products produced thereby. Said active complex for the skin consists of between 0.5 and 9 wt. % of creatine or a creatine derivative, between 0.1 and 40 wt. % of water-soluble glycogen, between 0.1 and 10 wt. % of a phospholipid, and between 0.1 and 5 wt. % of a cosmetically acceptable gel, water making up the remainder of the 100 wt. %, said mixture of creatine, glycogen and phospholipid being homogeneously distributed in the aqueous gel.

9 Claims, No Drawings

REVITALISING ACTIVE COMPLEX FOR THE SKIN

CROSS REFERENCE TO RELATED APPLICATION

This application is a national stage of PCT/DE02/00363 filed Jan. 29, 2002 and based upon DE 101 06 288.5 filed Feb. 2, 2001 under the International Convention.

BACKGROUND OF THE INVENTION

The invention relates to a revitalizing active complex for the skin and cosmetic products produced thereby.

BRIEF DESCRIPTION OF THE RELATED ART

DE-A-19841395 discloses the use of creatine or creatine derivatives as moisturizing substances in cosmetic preparations. Relevant products can be taken orally or applied locally onto the skin. Local application onto the skin is intended to counteract drying-out of the skin.

It is also known to use certain glucans in cosmetic preparations. According to DE-A-19911058, fine β-(1,3)-glucans are used to improve resorption into the stratum corneum of the skin. β-D glucan obtained from cereals is used to treat burns and scars according to WO99/21531. DE-A-19860371 proposes the use of water-insoluble linear polyglucans for achieving a particularly pleasant feeling on the skin.

SUMMARY OF THE INVENTION

The object of the invention is to provide new cosmetic products having a considerably improved effect regarding revitalization of the skin in particular.

According to the invention, a revitalizing active complex for the skin is provided. The complex consists of 0.5 to 9 wt. % of creatine or a creatine derivative,
0.1 to 40 wt. % of water-soluble glycogen,
0.1 to 10 wt. % of a phospholipid,
0.1 to 5 wt. % of a cosmetically acceptable gel, and water making up the remainder of the 100 wt. %, where the mixture of creatine, glycogen and phospholipid is homogeneously distributed in the aqueous gel.

Creatine (or N-carbamidoyl-N-methylglycine), which dissolves into creatinine (2-imino-1-methylimidazolidine-4-on) in an aqueous solution, is usually found in the muscle liquid of vertebrates and is contained, e.g. in meat extracts. Creatine derivatives include, e.g. creatine phosphate, creatine citrate or creatine pyruvate or mixtures thereof. Creatine ascorbate and creatine monohydrate can also be used, but they are not preferred.

Glycogen belongs to the branched glucans and is an α-D-1,4-glucan branched via α-1,6 bonds. It can be obtained from muscle tissue or from yeasts. It is preferred that a glycogen be used for the invention whose density is approximately 1.14 at 20° C., which has a refractive index of between 1.399 and 1.404 at 20° C. and a dry extract of between 39.0 and 48.0 % (weighed-in quantity: 5 g), the product Dermosaccharides GY® of maritime origin being particularly preferred. The glycogen's molecular weight is preferably between $2.7 \cdot 10^6$ and $1 \cdot 10^8$ daltons.

It is preferred that glycogen be contained in an amount ranging from 0.5 to 15 wt. %.

Phospholipids that can be used include, e.g. phosphatidylcholine, phosphatidylethanolamine, phosphatidyl-inositol, phosphatidylserine, phosphatidic acid and lysolecithins as well as mixtures thereof. Known products are, e.g. Phospholipon®80/80H, Phospholipon®90G/H.

It is preferred that the phospholipids be contained in an amount ranging from 0.5 to 8 wt. %.

Suitable gel-forming agents for the gel contained in the active complex include carbomer, xanthan gum, carrageenan, acacia gum, guar gum, agar-agar, alginate and tylosen, carboxymethyl cellulose, hydroxyethyl cellulose, quaternised cellulose, quaternised guar, certain polyacrylates, polyvinyl alcohol, poly-vinylpyrrolidone, and montmorillonite. Carbomer and guar gum are preferred.

The active complex according to the invention reduces the production of LDH (LDH=lacticodeshydrogenase, a stress enzyme produced by the cells when exposed to UV-B radiation). In addition, treatment with the aforesaid complex increases the cells' oxygen consumption, which is an indicator of the cells' vitality, and brings about a cell repair process which makes the cells look younger and improves their visual appearance.

Surprisingly, the aforesaid effect is a synergetic effect since the sum of the separate effects of glycogen and creatine is clearly surpassed, both in the anti-UV test and in the oxygen consumption test. In addition, it was surprisingly found that the synergy can be increased even further by adding 0.05 to 10 wt. % of a β-(1,3)-glucan obtained from yeast, e.g. baker's yeast or brewer's yeast, by means of an ultrasonic decomposition process according to U.S. Pat. No. 5,629,185. In the aforesaid process, a yeast suspension is passed through an ultrasonic exposure area in an ultrasonic flow-through cell, with a sonotrode extending into the flow-through cell up to half or two thirds of its length and is then immersed in the medium to be exposed to ultrasound. The center line of the sonotrode is arranged at an angle of between 80.5° and 88.5° relative to the plane in which the suspension enters the cell, and the ratio of the sonotrode's immersed length in mm to the volume exposed to ultrasound in ml is adjusted to a value of between 1:1.1 and 1:20. The amount of solid matter contained in the medium to be exposed to ultrasound ranges from 1:0.02 to 1:2.2 (in wt. %).

The active complex according to the invention can be contained in cosmetic preparations in an amount ranging from 0.01 to 22 wt. %, preferably 0.5 to 12 wt. %, particularly 1 to 8 wt. %. Such preparations include e.g. sun creams, sun gels, after-sun products, day creams, night creams, masks, body lotions, cleansing milk, make-ups, lipsticks, eye cosmetics, hair masks, hair conditioners, hair shampoos, shower gels, shower oils and bath oils. The aforesaid products are manufactured in a way known to those skilled in the art.

Usually, the aforesaid preparations contain further carrier substances and/or auxiliaries and, in some cases, further active agents, e.g. water, preservatives, vitamins, colorants, pigments having a coloring effect, scavengers, thickeners, emollients, moisturizing substances, fragrances, alcohols, polyols, esters, electrolytes, polar and non-polar oils, polymers, copolymers, emulsifiers, waxes and stabilizers.

Cosmetic active agents include, e.g. emulsifiers, inorganic and organic sunscreens, scavengers, moisturizing substances, vitamins, enzymes, plant-based active agents, polymers, melanin, antioxidants, anti-inflammatory natural active agents, fluorocarbons loaded with oxygen, asymmetric lamellar aggregates loaded with oxygen according to WO94/00109, kaolin and kaolin modified with $SiO_2$ according to WO94/17588, and amounts of a product obtained by gently decomposing a vegetable or animal starting material in an aqueous medium and subsequently condensing it with a substoichiometric amount of a $C_{10}$–$C_{20}$ fatty acid halogenide according to WO96/29048.

Further, emollients can be used, such as stearyl alcohol, glyceryl monoricinoleate, glyceryl monostearate, propane-1,2-diol, butane-1,3-diol, cetyl alcohol, isopropyl isostearate, stearic acid, isobutyl palmitate, oleyl alcohol, isopropyl laurate, decyl oleate, octadecane-2-ol, isocetyl alcohol, cetyl palmitate, silicone oils such as dimethyl polysiloxane, isopropyl myristate, isopropyl palmitate, polyethylene glycol, lanolin, cocoa butter, vegetable oils such as maize oil, cotton seed oil, olive oil, butyl myristate, palmitic acid, etc.

It can be advantageous that the only additional substances contained in the cosmetic preparations containing the active complex according to the invention are fluorocarbons loaded with oxygen or asymmetric lamellar aggregates. These aggregates consist of phospholipids and fluorocarbons or fluorocarbon mixtures loaded with oxygen. Such asymmetric lamellar aggregates are disclosed, e.g. in DE-B-42 21 255 or U.S. Pat. No. 5,643,601. They contain fluorocarbons, such as perfluorodecaline, in an amount ranging from 0.2 to 100% by weight/volume, the phospholipid having a phosphatidylcholine content of more than 30 and up to 99 wt. % and the degree to which the aforesaid aggregates penetrate into the skin depending on the critical solubility temperature of the fluorocarbons.

The aforesaid aggregates carry oxygen which enables the oxygen to penetrate into the skin and, as a consequence, deliver an improved oxygen supply to the skin. The said aggregates are manufactured by means of high-pressure homogenization of phospho-lipids, such as soy lecithin or egg lecithin or partly hydrogenated phospholipids, having a phosphatidylcholine content of more than 30 and up to 99 wt. % with perfluorinated or highly fluorinated carbon compounds or mixtures thereof which are able to transport gases, such as oxygen and carbon dioxide. Besides phosphatidylcholine, the aforesaid aggregates can also contain lysolecithins in a concentration ranging from 0.1 to 10 wt. % and/or charged phospholipids, such as phosphatidylethanolamine, n-acetylphosphatidylethanolamine or phosphatidic acid, in a concentration ranging from 0.1 to 30 wt. %, both concentrations relative to the aggregates' total weight.

The aggregates can be contained in an amount ranging from 0.5 to 40 wt. % relative to the cosmetic preparation, advantageously in an amount ranging from 2 to 15 wt. %, and particularly from 2 to 10 wt. %.

Another active agent that can be contained in a cosmetic preparation along with the active complex of the invention, either along with or without the aforesaid lamellar aggregates, is finely distributed magnetically hard single-range particles (single-crystals) having a high coercivity of between 3,000 and 5,000 oerstedts, and having particle sizes ranging from 50 to 1,200 nm. The magnetically hard particles are, for example, barium hexa-ferrite and/or strontium hexaferrite manufactured using the glass crystallization technique, i.e. by growing single-crystals from a quenched glass melt (see U.S. Pat. No. 5,800,835; U.S. Pat. No. 5,919,490).

The magnetically hard particles, which preferably have a particle size between 50 and 250 nm, can be present in an amount ranging from 0.5 to 10 wt. % relative to the cosmetic preparation, advantageously in an amount ranging from 1 to 8 wt. %, and particularly from 1 to 5 wt. %.

In a particularly preferred embodiment of the invention, the active complex according to the invention is present in a cosmetic preparation along with asymmetric lamellar aggregates loaded with oxygen and magnetically hard particles.

Another embodiment of the invention can be when the active complex according to the invention is present in a cosmetic preparation along with another complex (Complex II). The Complex II is characterized by an aqueous gel base that contains an encapsulated extract obtained by means of an aqueous extraction of pineapple fruit and the residue of an aqueous extraction of yogurt. Both extraction processes are carried out at a temperature ranging from 10° to 30° C., and the ratio of pineapple extract to yogurt residue ranges from 20:80 to 80:20.

Advantageously, the pineapple extract is encapsulated in liposomes, particularly in phospholipid liposomes.

The ratio of pineapple extract to yogurt residue is in the range from 40:60 to 60:40.

Advantageously, Complex II contains bromelin in an amount ranging from 0.1 to 1 wt. %.

Complex II can be provided in the cosmetic preparation in an amount ranging from 0.1 to 10 wt. % relative to the total weight of the preparation.

The synergetic effect of the active complex according to the invention can be proved by means of an in-vitro anti-stress test under UV activity. In this test, a culture of dermal fibroblasts obtained from explanted normal human skin is subjected to UV-induced stress. The amounts of the enzyme lacticodes-hydrogenase (LDH) produced as a consequence of the aforesaid stress are proportional to the cell damage caused. The culture medium contained, for example, 3 wt. % of glycogen (Dermo-saccharides GY®), and a series of control tests without the aforesaid additive was carried out for comparative purposes.

If the protection for the control group was assumed to be 100%, the addition of glycogen resulted in a 128% protection of those cells that were still alive 4 days after the UV radiation.

In the same way, 2 wt. % of creatine was added to the culture liquid, and a 110% protection was achieved compared to the control group.

A culture liquid containing 3 wt. % of glycogen and 2 wt. % of creatine brought about a protection of 153% thus clearly surpassing the result which had to be expected according to a simple summation. All values are mean values determined on the basis of 5 tests.

The further addition of 1.5 wt. % of β-(1,3)-glucan obtained by means of the aforementioned ultrasonic decomposition of baker's yeast led to a 171% protection.

Another synergy could be observed with regard to oxygraphy, i.e. the stimulation of the oxygen consumption of a cell homogenate of epithelial cells. Compared to the oxygen consumption of a control liquid (buffer), which was assumed to be 100%, the oxygen consumption increased up to 135% if 3 wt. % of glycogen was added to the control liquid. The addition of 2 wt. % of creatine brought about an increase in oxygen consumption up to 119%. If 3 wt. % of glycogen along with 2 wt. % of creatine was added, a 174% oxygen consumption was achieved.

The addition of 1.5 wt. % of β-(1,3)-glucan obtained by means of the aforementioned ultrasonic decomposition of baker's yeast led to an increase in oxygen consumption up to 191%.

The results clearly demonstrate the existence of a synergy which could not be expected and which considerably improves cell revitalization.

The invention will hereinafter be explained in more detail by means of examples. All quantities are in weight percent if not indicated otherwise.

EXAMPLE 1

Preparation of the Active Complex

EXAMPLE 1A

| | |
|---|---|
| Creapure Pyruvate ® | 9 |
| Phospholipon ® 80 | 5 |
| carbomer | 2 |
| water | ad 100 |
| Dermosaccharides GY ® (glycogen) | 5 |
| triethanolamine (TEA) | 0.2 |

The creatine pyruvate and the phospholipid were mixed with each other and combined at a high rotational speed of approximately 15,000 rpm until liposomes were obtained. In a separate step, the gel was stirred into water and homogenized as well. Subsequently, the homogenized mixture of creatine derivative and phospholipid was stirred into the aqueous gel and neutralized with TEA. Glycogen and, if desired, glucan obtained from yeast were stirred into the aforesaid mixture, and the mixture was homogenized at 10,000 rpm until a homogeneous product was obtained.

EXAMPLES 1b) to 1e)

8 wt. % of Creatine Phosphate (Example 1b), 5 wt. % of Creatine Citrate (Example 1c), 3 wt. % of Creatine Phosphate (Example 1d) and 7 wt. % of pure creatine (Example 1e) was used instead of Creatine Pyruvate, and in addition 1.5 wt. % of glucan obtained by means of the aforementioned yeast decomposition process was added in Example 1d).

EXAMPLE 2

Cosmetic Cream

| | |
|---|---|
| Phase A | |
| water | ad 100 |
| propylene glycol | 2 |
| xanthan gum | 0.5 |
| Phase B | |
| stearine acid | 0.5 |
| stearic acid | 1 |
| cetyl alcohol | 2 |
| cetearyl alcohol | 5 |
| Phase C | |
| vitamin E | 1 |
| active complex according to Example 1a) | 2 |
| perfume | 0.5 |
| preservative | 1 |

Phase A and Phase B were heated separately up to approximately 80° C. Phase B was stirred into Phase A, and the mixture was homogenized for 20 minutes and cooled down to approximately 35° C. while stirring. Subsequently, Phase C was added, and the mixture was homogenized again. The mixture was cooled down to 28-30° C. while stirring.

EXAMPLE 3

Body Lotion

| | |
|---|---|
| Phase A | |
| water | ad 100 |
| propylene glycol | 5 |
| xanthan gum | 0.1 |
| Phase B | |
| PEG 40 stearate | 1.5 |
| cetyl alcohol | 0.5 |
| cetearyl alcohol | 0.5 |
| Phase C | |
| active complex according to Example 1e) | 12 |
| silicone oil | 2.5 |
| perfume | 0.5 |
| preservative | 1 |

Processing was done as in Example 2.

EXAMPLE 4

Cream for Sensitive Skin

| | |
|---|---|
| Phase A | |
| water | ad 100 |
| glycerine | 3 |
| crosspolymer | 0.2 |
| Phase B | |
| steareth 21 | 3.5 |
| steareth 2 | 2.5 |
| cetyl alcohol | 2 |
| Phase C | |
| triethanolamine | 0.2 |
| Phase D | |
| dicapryl ether | 5 |
| preservative | 1 |
| Phase E | |
| active complex according to Example 1c) | 10 |
| asymmetric lamellar aggregates according to Example 1 of US-A-5643601 | 5 |
| perfume | 0.8 |

Phase A and Phase B were heated separately up to approximately 70° C. Phase B was stirred into Phase A, and the mixture was homogenized for 20 minutes and cooled down to approximately 50° C. while stirring. Phase C was then added, and the mixture was cooled down to 40° C. Subsequently, Phase D was added, the mixture was homogenized again and then combined with Phase E at approximately 35° C. and stirred thoroughly.

EXAMPLE 5

Make-Up

| | |
|---|---|
| Phase A | |
| water | ad 100 |
| glycerine | 2.5 |
| crosspolymer | 0.3 |
| Phase B | |
| steareth 21 | 2.3 |
| steareth 2 | 1.8 |
| cetyl alcohol | 3.8 |
| Phase C | |
| triethanolamine | 0.3 |
| Phase D | |
| silicone | 5 |
| preservative | 1 |
| Phase E | |
| active complex according to Example 1b) | 19 |
| suspension of magnetically hard particles according to Example 1 of US-A-5800835, particle size 180 nm | 1 |
| perfume | 0.6 |
| coloring pigments | 5 |

Processing was done as in Example 4.

EXAMPLE 6

Shower Gel

| | |
|---|---|
| water | ad 100 |
| crosspolymer | 0.5 |
| sodium laureth sulfate | 20 |
| cocoamidopropyl betaine | 10 |
| quaternium 80 | 1 |
| active complex according to Example 1d) | 8 |
| complex II contained in liposomes[1] | 1 |
| perfume oil | 1 |
| preservative | 1 |

The ingredients were combined to form a mixture by stirring them into one another, one after the other, at room temperature (approximately 25° C.).

Pineapple fruit extract and residue of an aqueous yogurt extract, ratio: 20:80; bromelin content of Complex II: 0.4 wt. %; produced according to Example 3 of DE-A-10042576.

We claim:

1. A revitalizing active complex for the skin, said complex comprises
    0.5 to 8 wt. % of creatine or a creatine derivative,
    0.1 to 40 wt. % of water-soluble glycogen,
    0.1 to 10 wt. % of a phospholipid,
    0.1 to 5 wt. % of a cosmetically acceptable gel, and water making up the remainder of the 100 wt. %, wherein the mixture of creatine, glycogen and phospholipid is homogeneously distributed in the aqueous gel.

2. An active complex according to claim 1, wherein the complex contains 0.05 to 10 wt. % of a β-(1,3)-glucan, wherein said β-(1,3)-glucan is obtained from yeast by means of an gentle ultrasonic decomposition process.

3. A cosmetic preparation comprising the active complex of claim 1, in an amount ranging from 0.1 to 22 wt. % relative to the total weight of the preparation.

4. A cosmetic preparation comprising the active complex of claim 1, in an amount ranging from 0.5 to 12 wt. %.

5. A cosmetic preparation comprising the active complex of claim 1, further comprising 0.5 to 15 wt. % of asymmetric lamellar aggregates,
    wherein said asymmetric lamellar aggregates comprise fluorocarbons and phospholipids, and
    where said asymmetric lamellar aggregates are loaded with oxygen.

6. A cosmetic preparation comprising the active complex of claim 1, further comprising 0.5 to 10 wt. % of magnetically hard single-crystals comprising barium hexaferrite and having a coercivity of between 3,000 and 5,000 oerstedts and having particle sizes ranging from 50 to 250 nm, and, optionally, 0.5 to 15 wt. % of asymmetric lamellar aggregates,
    wherein said asymmetric lemallar aggregates comprise fluorocarbons and phospholipids, and
    where said asymmetric lamellar aggregates are loaded with oxygen.

7. A cosmetic preparation comprising the active complex of claim 1, further comprising 0.1 to 10 wt. % of a second complex consisting of a) an aqueous gel base which contains an encapsulated extract obtained by means of an aqueous extraction of pineapple fruit and b) the residue of an aqueous extraction of yogurt, wherein both extraction processes are carried out at a temperature ranging from 10 to 30° C. and wherein the ratio of pineapple extract to yogurt residue ranges from 20:80 to 80:20.

8. A cosmetic preparation comprising a revitalizing active complex for the skin, said complex comprises
    0.5 to 8 wt. % of creatine or a creatine derivative,
    0.1 to 40 wt. % of water-soluble glycogen,
    0.1 to 10 wt. % of a phospholipid,
    0.1 to 5 wt. of a cosmetically acceptable gel, and water making up the remainder of the 100 wt. %,
    wherein the mixture of creatine, glycogen and phospholipid is homogeneously distributed in the aqueous gel, and
    wherein said cosmetic preparation is a cosmetic gel, a cream, a lotion, a make-up or a stick.

9. A cosmetic preparation according to claim 8, wherein said cosmetic preparation contains an inorganic or organic sunscreen.

* * * * *